United States Patent
Ouchi

(10) Patent No.: US 8,981,303 B2
(45) Date of Patent: Mar. 17, 2015

(54) SENSOR DEVICE

(71) Applicant: Canon Kabushiki Kaisha, Tokyo (JP)

(72) Inventor: Toshihiko Ouchi, Machida (JP)

(73) Assignee: Canon Kabushiki Kaisha, Tokyo (JP)

(*) Notice: Subject to any disclaimer, the term of this patent is extended or adjusted under 35 U.S.C. 154(b) by 92 days.

(21) Appl. No.: 13/795,978

(22) Filed: Mar. 12, 2013

(65) Prior Publication Data
US 2013/0240740 A1     Sep. 19, 2013

(30) Foreign Application Priority Data

Mar. 13, 2012   (JP) ................ 2012-056533

(51) Int. Cl.
| | | |
|---|---|---|
| *G01J 5/08* | (2006.01) | |
| *G01J 3/10* | (2006.01) | |
| *G01J 3/42* | (2006.01) | |
| *G01N 21/3581* | (2014.01) | |
| *G01N 21/552* | (2014.01) | |
| *G01N 21/3586* | (2014.01) | |

(52) U.S. Cl.
CPC .......... *G01J 5/0818* (2013.01); *G01J 3/108* (2013.01); *G01J 3/42* (2013.01); *G01N 21/3581* (2013.01); *G01N 21/553* (2013.01); *G01N 21/3586* (2013.01)
USPC ...................................... 250/353

(58) Field of Classification Search
CPC ..................................................... G01J 5/08
USPC ...................................... 250/353
See application file for complete search history.

(56) References Cited

U.S. PATENT DOCUMENTS

| | | |
|---|---|---|
| 5,349,598 A | 9/1994 | Ouchi et al. |
| 5,594,577 A | 1/1997 | Majima et al. |
| 5,654,814 A | 8/1997 | Ouchi et al. |
| 5,742,418 A | 4/1998 | Mizutani et al. |
| 5,757,828 A | 5/1998 | Ouchi |
| 6,597,713 B2 | 7/2003 | Ouchi |
| 7,151,865 B2 | 12/2006 | Ouchi |
| 8,170,386 B2 | 5/2012 | Katagiri et al. |
| 2005/0242287 A1* | 11/2005 | Hakimi .................. 250/363.09 |
| 2008/0265165 A1* | 10/2008 | Yeh et al. ................... 250/341.1 |

FOREIGN PATENT DOCUMENTS

JP     2010-204488 A     9/2010

OTHER PUBLICATIONS

Hebling et al., "Generation of High-Power Terahertz Pulses by Tilted-Pulse-Front Excitation and Their Application Possibilities", J. Opt. Soc. Am. B/vol. 25, No. 7/Jul. 2008, pp. B6-B19.

* cited by examiner

*Primary Examiner* — David Porta
*Assistant Examiner* — Hugh H Maupin
(74) *Attorney, Agent, or Firm* — Fitzpatrick, Cella, Harper & Scinto

(57) ABSTRACT

A sensor device has an optical waveguide containing an electro-optic crystal for propagating light, a coupler provided adjacent to the optical waveguide to propagate a terahertz wave generated from the electro-optic crystal as a result of the propagation of light in the optical waveguide, and a detector for detecting the terahertz wave propagating through the coupler or the light propagating through the optical waveguide. The terahertz wave is totally reflected in a section of the coupler opposite to a section where the coupler is adjacent to the optical waveguide while passing through and propagating in the optical waveguide, and in the total reflection section, the terahertz wave interacts with a subject placed close to the total reflection section.

19 Claims, 4 Drawing Sheets

SENSOR DEVICE

BACKGROUND OF THE INVENTION

1. Field of the Invention

The present invention relates to a sensor device using a terahertz wave containing electromagnetic wave components in a frequency domain from a millimeter wave band to a terahertz wave band (not less than 30 GHz and not more than 30 THz), and a sensing system or an imaging system using the same.

2. Description of the Related Art

Recently, non-destructive sensing technology using terahertz waves (THz waves) has been developed. As an application field of electromagnetic waves in this frequency band, there is technology for safe fluoroscopic inspection equipment as an alternative to X-ray equipment to perform imaging. Further, there have been developed spectroscopic technology for determining the absorption spectrum or complex permittivity inside a substance to examine physical properties such as the bonding state of molecules, measurement technology for examining physical properties, such as carrier concentration or mobility, and electric conductivity, and biomolecule analysis technology. As the method of generating a terahertz wave, a method using nonlinear optical crystal is widely used. Typical nonlinear optical crystals include LiNbOx (hereinafter, also referred to as LN), LiTaOx, NbTaOx, KTP, DAST, ZnTe, GaSe, GaP, and CdTe. Second-order nonlinear phenomena are used for generation of a terahertz wave. As a system, there is known difference-frequency generation (DFG) using incidence of two laser beams having a frequency difference. In the DFG system, when two laser beams different in frequency are entered, nonlinear polarization having a cycle corresponding to a difference frequency of the two laser beams occurs. In the nonlinear optical crystal, the energy state is excited by the incidence of the laser beams and an energy wave is radiated when returning to the original energy state. When the nonlinear optical crystal is nonlinearly polarized, an energy wave corresponding to the polarized frequency is radiated, while when it is polarized with a frequency of a terahertz wave, the terahertz wave is radiated from the nonlinear optical crystal. There are also known a system for generating a monochromatic terahertz wave by an optical parametric process, and a system for generating a terahertz wave pulse by optical rectification with radiation of a femtosecond pulsed laser beam.

As a process of generating a terahertz wave from such nonlinear optical crystal, electro-optic Cerenkov radiation has recently drawn attention. This is a phenomenon in which, as illustrated in FIG. 8, a terahertz wave 101 is radiated in a conical shape like a shock wave when a group velocity of propagation of a laser beam 100 as an excitation source is faster than a propagation phase velocity of the generated terahertz wave. A radiation angle $\theta_c$ (also called "Cerenkov angle") of the terahertz wave is determined by the following equation according to a ratio of refractive indexes in a medium (nonlinear optical crystal) between light and the terahertz wave:

$$\cos \theta_c = v_{THz}/v_g = n_g/n_{THz} \qquad (1).$$

where $v_g$ and $n_g$ denote the group velocity and group refractive index, respectively, and $v_{THz}$ and $n_{THz}$ denote the phase velocity and refractive index of the terahertz wave, respectively. Up to now, there has been reported that a high-intensity terahertz pulse is generated by optical rectification using the Cerenkov radiation phenomenon by entering a femtosecond laser beam with inclined wavefront into LN (J. Opt. Soc. Am. B, vol. 25, pp. B6-B19, 2008). Further, it is described that a monochromatic terahertz wave is generated by a DFG system using a slab waveguide having a thickness sufficiently smaller than the wavelength of the generated terahertz wave to eliminate the necessity of wavefront tilt (Japanese Patent Application Laid-Open No. 2010-204488 (Patent Document 1)).

The examples described in the aforementioned conventional art documents are related to a proposal of performing phase matching in the radiation direction between terahertz waves generated from different wave sources because the terahertz waves are generated by traveling-wave excitation to reinforce the terahertz waves with each other in order to improve extraction efficiency. A terahertz wave generated from a slab waveguide propagates in an adjacent coupler (Si prism in the case of Patent Document 1) and is extracted from the coupler into a space. The features of this radiation system include the fact that a high-intensity terahertz wave can be generated with relatively high efficiency among those using nonlinear optical crystal, and the fact that the terahertz wave band can be widened by selecting absorption in a terahertz region due to a phonon resonance unique to the crystal on a high frequency side. Compared with terahertz generation by a photoconductive device, these techniques can widen the generation band, and in the case of generating a terahertz wave pulse with optical rectification, the pulse width can be reduced. Therefore, it is expected that the device performance can be improved when the device is used in a terahertz time-domain spectroscopic apparatus, for example.

However, in the systems described in the aforementioned conventional art documents, Cerenkov radiation of a terahertz wave generated in nonlinear optical crystal (which is the term used in these documents, and in this specification, the term "electro-optic crystal" as an approximately equivalent term is used) and propagating in the coupler is all extracted into a space. Then, light is focused on a sample desired to be sensed as necessary by means of a parabolic mirror or a lens to analyze a microscopic region of the sample. In this case, since the wavelength of a terahertz wave used is typically about a few hundred µm, light can only be condensed up to a beam diameter corresponding to the wavelength due to the diffraction limitation. The reality is that the spatial resolution is generally in millimeters though it depends on the optical system. This makes it difficult to sense a microscopic sample or to deal with imaging of a component distribution at a resolution equal to or less than the wavelength. To respond to a request for observation at an improved spatial resolution, it is necessary to use known near field technology in an optical region.

SUMMARY OF THE INVENTION

In one aspect of the present invention, a sensor device has an optical waveguide containing electro-optic crystal for propagating light, a coupler provided adjacent to the optical waveguide to propagate a terahertz wave generated from the electro-optic crystal as a result of the propagation of light in the optical waveguide, and a detector for detecting the terahertz wave propagating through the coupler or the light propagating through the optical waveguide, wherein the terahertz wave is totally reflected in a section of the coupler opposite to a section where the coupler is adjacent to the optical waveguide while passing through and propagating in the optical waveguide, and in the total reflection section, the terahertz wave interacts with a subject placed close to the total reflection section.

According to one aspect of the present invention, the sensor device is so designed that the terahertz wave interacts with the subject in the total reflection section of the coupler, so that a microscopic region equal to or less than the wavelength can be analyzed by using the terahertz wave. Thus, for example, a minute amount of sample can be analyzed or the subject can be scanned by attaching the sensor device at one end of a probe, resulting in imaging at high spatial resolution.

Further features of the present invention will become apparent from the following description of exemplary embodiments with reference to the attached drawings.

DESCRIPTION OF THE EMBODIMENTS

Figure 1:
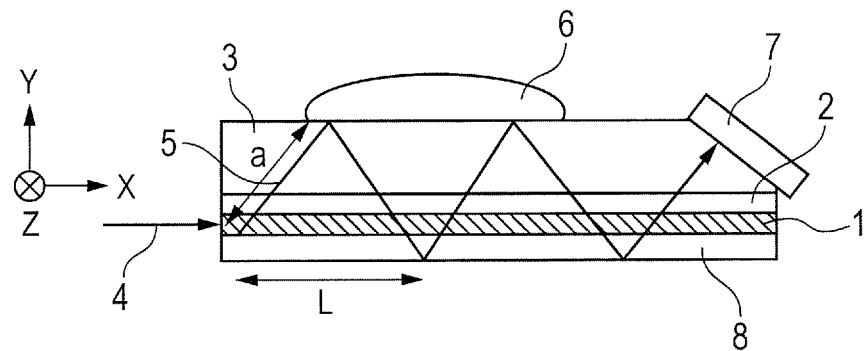
FIG. 1 is a structural diagram of a sensor device according to Embodiment 1 of the present invention.

Preferred embodiments of the present invention will now be described in detail in accordance with the accompanying drawings.

In a sensor device having an optical waveguide containing electro-optic crystal according to the present invention, a terahertz wave is totally reflected by an interface between a coupler for extracting the terahertz wave generated by light propagating through the optical waveguide and the outer side of the coupler to propagate in the coupler. Then, the terahertz wave propagating through the coupler or the light propagating through the optical waveguide is detected. When the terahertz wave propagating through the coupler is detected, a measurement sample is placed on an interface with the coupler where the terahertz wave is totally reflected so that a detector will detect that the propagation state of the terahertz wave in the coupler varies. On the other hand, when the light propagating through the optical waveguide is detected, the detector detects changes in the propagated light interacting with the terahertz wave the propagation state of which varies to acquire sample information. The variations in the propagation state of the THz wave occur in such a manner that the THz wave is totally reflected in a section of the coupler opposite to a section of the coupler adjacent to the optical waveguide while passing through and propagating in the optical waveguide, and in the total reflection section, the THz wave interacts with a subject placed close to the total reflection section. In this specification, the terms "sample" and "subject" are used as almost synonymous terms to express an object to be sensed.

In the above structure, an evanescent field of the terahertz wave is formed close to the totally reflecting interface, and the electric field does not generally penetrate the outside of the coupler beyond a distance about one tenth of the wavelength (wavelength of the terahertz wave in a free space). Note that this penetration depth exactly follows a known theoretical formula determined by the refractive indexes of two mediums that form the interface, and the incident angle and wavelength of a totally reflected electromagnetic wave with respect to the interface. Therefore, it is necessary to place the sample to almost contact or contact with the totally reflecting interface, i.e., to put the sample close to the totally reflecting interface up to a distance of the penetration of the electric field (penetration depth) or less. This "almost contact" may be direct or indirect through a film of glass or resin. Further, an aperture corresponding to the wavelength or less (see a window structure in FIG. 4 to be described later) is provided as necessary so that imaging at a spatial resolution of the wavelength or less can be performed. The coupler is provided adjacent to the optical waveguide so that the terahertz wave generated in the optical waveguide can be extracted into the coupler. The meaning of this term "adjacent" is defined from the standpoint of the degree of intensity attenuation of propagation light at least on the interface between the coupler and the optical waveguide as will be described later.

Exemplary embodiments and examples will now be described below with reference to the accompanying drawings.

(Embodiment 1)

A terahertz sensor device made of LN crystal (one kind of electro-optic crystal already illustrated) according to Embodiment 1 of the present invention will be described with reference to FIG. 1. In FIG. 1, a layer 1 made of MgO doped LN crystal is sandwiched between two low refractive layers 2 and 8 as oxide film layers or resin layers to form a slab optical waveguide. This is an optical waveguide containing electro-optic crystal for propagating light. The thicknesses of the respective layers are typically as follows: The LN crystal layer is 3.8 μm, and the low refractive layer is 0.5 μm to 2.5 μm. These thicknesses can be designed according to the necessary terahertz wave band in a manner to be described later, but the thicknesses are not limited to these values. The orientation of the LN crystal is determined by transferring a Y-cut LN crystal substrate to a Si substrate (including processes such as adhesion and grinding so that the propagation direction of incident light 4 will be X axis and the upward direction in FIG. 1 will be Y axis. This is because, when the direction of the electric field of the incident light 4 illustrated in FIG. 1 is z-axis normal to the plane of paper, the electric field acts on z-axis where the nonlinear coefficient of the LN crystal is large to maximize the generation efficiency of the terahertz wave. However, the orientation of the LN crystal may be any other crystal orientation.

Such a structure can efficiently generate the terahertz wave by electro-optic Cerenkov radiation as the second-order nonlinear phenomena. The generated terahertz wave is intensified in a direction where the Cherenkov angle determined by a difference in refractive index between light and the terahertz wave in the LN crystal is about 65 degrees. However, as will be described later, if the coupler made of a material having a refractive index with which the terahertz wave can propagate properly is arranged adjacent to the optical waveguide, the direction will be substantially determined by a ratio between the group velocity of the terahertz wave in the material and the group velocity of light in the optical waveguide.

As in FIG. 1, a coupler 3 for propagation of the terahertz wave is arranged adjacently on the upper surface of the low refractive layer 2. Thus, the coupler 3 is provided adjacent to the optical waveguide so that light will propagate in the optical waveguide to propagate the terahertz wave generated from the electro-optic crystal. Here, Si is suitably used for the coupler in terms of the magnitude of the refractive index and low loss of the terahertz wave, but the material is not limited thereto. In this embodiment, an ultrashort pulse laser beam of about 100 fs is typically entered into the optical waveguide to generate a terahertz wave pulse from the optical waveguide containing the LN crystal by the optical rectification effects. It is desired that the pulse width be narrowed because the peak intensity increases as the pulse width becomes narrower to enhance the nonlinear phenomenon. In a practice, a pulse width of 30 fs or less is suitably used. At this time, as described in the Related Art, a strong terahertz wave is generated noncollinearly along with the propagation of light according to the above equation (1) (see a path 5 of the terahertz wave in FIG. 1). As mentioned above, in the case of a combination of the LN crystal in the optical waveguide and the Si coupler, the Cherenkov angle is about $\theta c=49$ degrees [$=\cos^{-1}$ (refractive index of light to the LN crystal/refractive index of Si to the THz wave)$=\cos^{-1}$ (2.2/3.4)] due to a difference in refractive index between respective materials. The total reflection critical angle from Si to space is about 17 degrees [$=\sin^{-1}$ (refractive index of air/refractive index of Si to the terahertz wave)$=\sin^{-1}$ (1/3.4)], which meets the total reflection condition on the interface with space even if the interface is a face parallel to the optical waveguide. On the other hand, even when being reflected on the substrate side, this does not have a big influence on the terahertz wave because the optical waveguide and the low refractive layer 8 are thin, resulting in total reflection as well. Thus, the above-mentioned Si substrate transferred from the LN crystal layer can be used intact as the coupler.

Thus, the terahertz wave propagates in a zig-zag manner as indicated by the path 5 in FIG. 1 to be totally reflected on an interface between the bottom part of the low refractive layer 8 and space while being partially penetrated into the interface between the coupler 3 and the space, and into the optical waveguide. At this time, it is desired to prevent the terahertz wave generated from the optical waveguide and the terahertz wave propagating while being totally reflected in the coupler from interfering with each other. In the case of use of the Si coupler for the LN crystal, if the propagation distance of light in the optical waveguide in FIG. 1 is denoted by L, a propagation distance $2a$ when the terahertz wave returns to the optical waveguide after being totally reflected on the interface between the coupler and the space is about 1.5 L (L/(2a)=cos 49 degrees). In this case, the difference in propagation time is as follows: Since the ratio between the refractive index of the LN crystal to the light and the refractive index of Si to the THz wave is 2.2:3.4, the ratio between the propagation velocities of $v_{light}$ and $v_{THzwave}$ becomes 3.4:2.2. Then, in regard to the propagation time to the same point, the THz wave is 1.5 $L/v_{THz\_wave}$ and the light is $L/v_{light}$, turning out that the former requires time 2.3 times as long as the latter (($1.5 L/v_{THz\_wave})/(L/v_{light})=1.5*3.4/2.2=2.3$). Therefore, in the structure of the embodiment, if light enters the optical waveguide intermittently at intervals of predetermined times or more in consideration of the difference, the interference of the generated terahertz wave to cause a signal disturbance can be avoided. Thus, the sensor device of the embodiment is so designed that the terahertz wave generated from the electro-optic crystal and the terahertz wave reflected in a total reflection section of the coupler will not interfere with each other.

Figure 2:
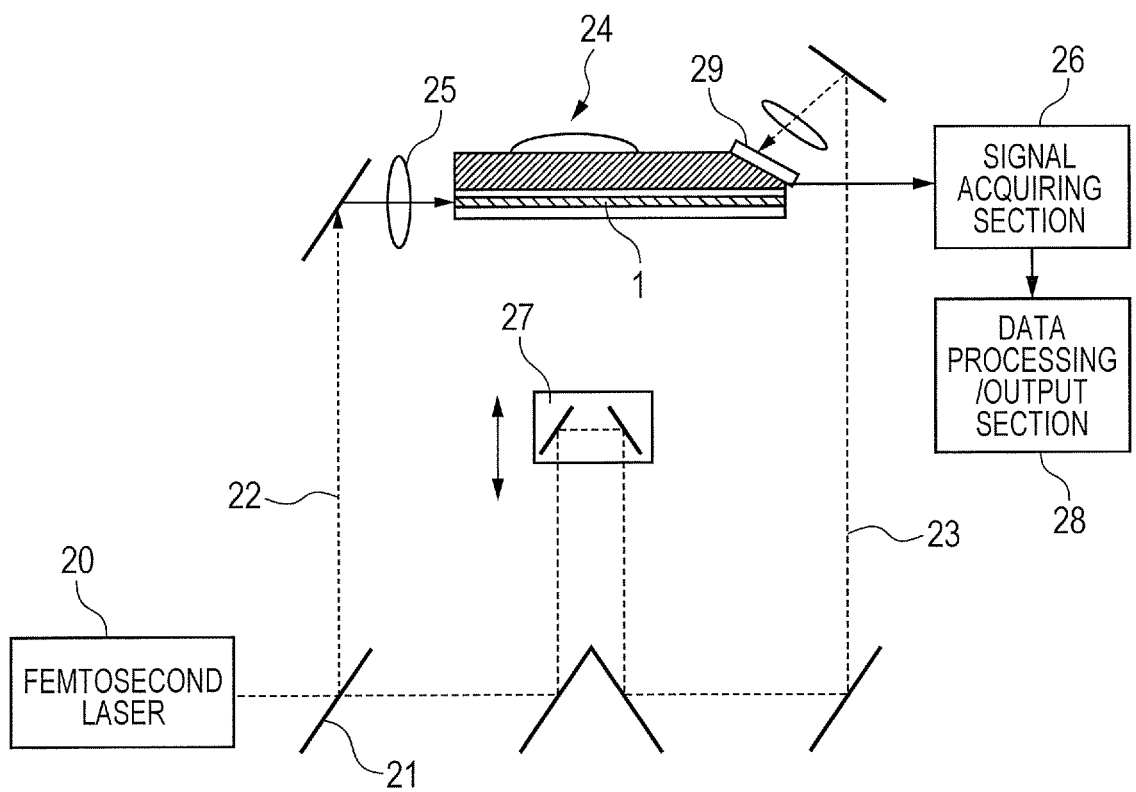
FIG. 2 is a block diagram of a terahertz time-domain spectroscopic apparatus according to Embodiment 1 of the present invention.

Suppose that the propagation distance is to be L=1 mm. In this case, the thickness d of the coupler 3 is designed to be d=0.58 mm from d/0.5=tan 49 degrees (the optical waveguide layer is ignored as being thin). As this thickness is comparable to that commonly available as Si wafer, it could be said that the thickness has a strength enough for the thin-film LN crystal to support the optical waveguide. The terahertz wave propagating through this coupler is converted to an electric signal by a terahertz wave detector 7 integrated at an end having a face where the propagated terahertz wave is not totally reflected. As the terahertz wave detector 7, for example, a known photoconductive device made of low-temperature grown GaAs can be used. Thus, a pulse waveform can be acquired in a terahertz time-domain spectroscopic apparatus (THz-TDS) as illustrated in FIG. 2.

It is also possible to use the electro-optic crystal to detect the terahertz wave. As illustrated in FIG. 1, it is desired that an end face not to meet a total reflection condition (e.g., to be normal to the Cherenkov angle of 49 degrees) be formed in an end portion of the coupler to paste the terahertz wave detector on this end face. Of course, there is a method in which the detector is bonded to a surface that meets the total reflection condition (not illustrated) without creating such a cut face to detect an evanescent wave directly. On the other hand, as mentioned above, there is another method in which a photodetector detects light propagating in the optical waveguide. In the case of a photodetector, a pin photo diode or the like may be pasted directly on the exit end face of the optical waveguide.

When the terahertz wave is folded several times as illustrated in FIG. 1, plural terahertz waves that reach the detector 7 late are detected for a single incident laser pulse. Since this depends on a difference in propagation time determined by the materials and thicknesses of respective elements described above, plural terahertz waves can be detected at time intervals determined for each individual sensor device if no sample is placed.

Figure 3:
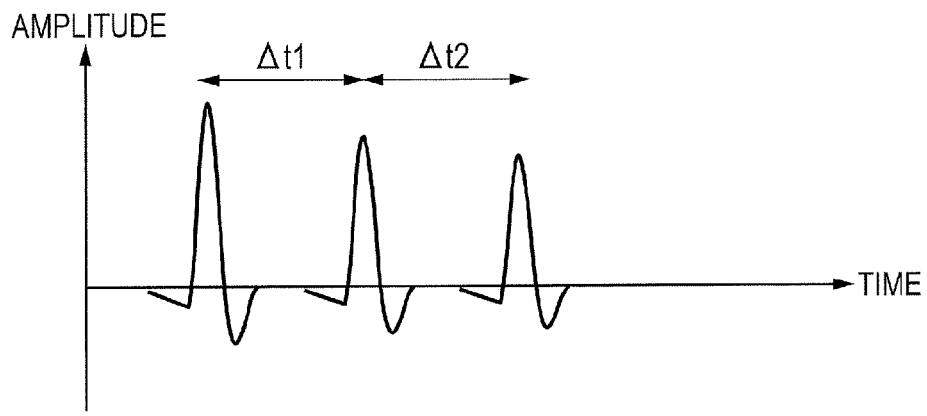
FIG. 3 is a chart illustrating an example of temporal waveform acquired in Embodiment 1.

When L=1 mm and the terahertz wave is reflected twice on the interface between the coupler and the space as illustrated in FIG. 1, a signal is detected twice at each time interval $\Delta t$ after a terahertz wave that reaches without being reflected even once. The time interval $\Delta t$ is a time for propagating a distance of a in FIG. 1. Since a=0.75 mm so far, a pulse time interval $\Delta t$=(refractive index of Si to the terahertz wave)×a/velocity of light=8.5 ps. In other words, a first pulse of terahertz wave propagates the distance a from the optical waveguide and directly reaches the detector 7. When the pulse is folded twice as illustrated in FIG. 1, a total of three pulses are observed at intervals of 8.5 ps (see FIG. 3). This time is a rough estimate when there is no sample, and an error occurs in practice (in this case, $\Delta t1=\Delta t2\approx 8.5$ ps in FIG. 3). In such a structural design, if a pulse of light having a duration of 8.5 ps or less is entered, the above-mentioned interference of the terahertz wave can be avoided. Since the duration of the incident pulse typically used in the embodiment is about 100 fs or less as mentioned above (the repetition is in MHz commonly used), no problem is found.

In this sensor device, when a measurement sample 6 is placed on the Si coupler 3 as illustrated in FIG. 1, second and third pulses reach the detector 7 while being deformed because of a difference in reflection coefficient due to a difference in complex permittivity of the sample upon reflection on a certain face of the sample. Since the first pulse reaches directly from the optical waveguide, the first pulse can be used as reference for observation of pulse modifications of the second and third pulses. In other words, in a method of sensing a terahertz wave using the sensor device of the present invention or a probe or a system to be described later, the following steps can be executed to acquire information on the properties of a subject: In a first step, a pulse signal of terahertz wave that is not subjected to total reflection in the coupler and a pulse signal of terahertz wave that is subjected to total reflection in the coupler are detected by the detector. In a second step, the signal that is not subjected to total reflection is compared with the signal that is subjected to total reflection. In a third step, from the comparison result in the comparison step, information on a change caused by the presence or absence of the placement of the subject in the total reflection section of the coupler is obtained to acquire the properties of the subject. In the case of the above double reflection type, the thickness of the Si coupler 3 is set to 0.58 mm as mentioned above and the length of the optical waveguide can be set, for example, to about 2.5 mm. Attempts of sample detection using the sensor device of the present invention will be described in an example later.

Here, the thickness of each layer will be described. The thickness necessary for an electro-optic crystal section of the optical waveguide is equal to or less than half the equivalent wavelength in the device to the maximum frequency of a terahertz wave to be extracted (i.e., such a thickness that does not cause cancellation of reversed phases after phase shifting corresponding to the thickness of a core portion 1 is reversed on the equiphase surface of the generated terahertz wave). On the other hand, it is desired that the thickness of each of the upper and lower low refractive layers 2 and 8 be thick enough to function as a clad layer during propagation of a laser beam through the optical waveguide and thin enough to be able to ignore the influence of multiple reflection or loss during propagation of the terahertz wave in the coupler 3. In the former case, it is desired that the light intensity on the interface with the coupler 3 in the optical waveguide having the low refractive layer 2 as a clad be equal to or more than a thickness equal to or less than $1/e^2$ (where e is a base of natural logarithm) of the light intensity in a region where the crystal 1 is a core region. The meaning of the above-mentioned term "adjacent" of the coupler to the optical waveguide is defined from this standpoint. In other words, the coupler is arranged adjacent to the optical waveguide so that the light intensity on the interface between the coupler and the optical waveguide will be as mentioned above.

In the latter case, it is desired that the thickness of the upper clad layer be a thickness of about one tenth of an equivalent wavelength $\lambda_{eq}$ (THz) of the terahertz wave in the low refractive layer 2 at the maximum frequency for external radiation. This is because any structure in the size one tenth of the wavelength is generically considered to be able to ignore the influences of reflection, scattering, and refraction on an electromagnetic wave of the wavelength. However, even beyond the desired thickness, it is possible to implement the function of the terahertz wave device of the present invention. The thicknesses of the LN crystal layer and the low refractive layers mentioned above are derived from this design concept. For example, if the device handles up to 7.6 THz (phonon absorption frequency of the LN crystal), the wavelength of the terahertz wave in the free space will be about 39.5 μm. Here, suppose that the refractive index of the terahertz wave in the crystal layer 1 is 5.2 (LN:MgO), and the refractive index of the upper and lower low refractive layer 2 and 8 to light is 1.5. From these, the thickness of the crystal layer 1 is designed to be 3.8 μm in this embodiment so that the thickness will be one-half of the equivalent wavelength $\lambda_{eq\_core}$ (about 39.5/5.2=7.6) or less. Further, the thickness of the clad layer is designed to be equal to or less than one tenth of $\lambda_{eq\_clad}$ (about 39.5/1.5=26.3), i.e., equal to or less than 2.6 μm. If the electro-optic crystal is changed to change the phonon absorption frequency, since the available terahertz wave band is changed, these thicknesses can be changed accordingly. Thus, the optical waveguide contains the electro-optic crystal as a core portion of light and the low refractive layers as a clad portion. In this case, when at least one layer of the low refractive layers is sandwiched between the electro-optic crystal and the coupler, the thickness d of at least one layer fulfills $a<d<\lambda_{eq}/10$, where a thickness that is $1/e^2$ of the intensity of light propagating in the electro-optic crystal is denoted by a, and the equivalent wavelength in at least one layer at the maximum frequency of the terahertz wave propagating in the coupler is denoted by $\lambda_{eq}$.

Although the design method and design values are described above in the specific example, the electro-optic crystal to form the optical waveguide used to generate a terahertz wave is not limited to the LN crystal. As described in the Related Art, LiTaOx, NbTaOx, KTP, DAST, ZnTe, GaSe, GaP, and CdTe can also be used as other kinds of electro-optic crystals. Likewise, Si is suitably used as the material used for the coupler, but any other material may be selected to make a combination of a coupler having a refractive index, with which the terahertz wave can propagate in the coupler, and the electro-optic crystal. For example, in the case of the LN crystal, Ge can also be used for the coupler. Further, the number of reflections of the terahertz wave, the thickness of the coupler, the length of the optical waveguide (though these have a constant relation as mentioned above) are not limited to those in the embodiment. For example, such a structure to increase or decrease the number of pulses can be designed by increasing or decreasing the number of reflections, i.e., by increasing or decreasing the ratio between the length of the optical waveguide and the thickness of the coupler, and such a structure to increase or decrease the pulse time intervals can be designed by increasing or decreasing the thickness of the coupler. The principles are as already described. Further, the specifications for the pulse width of a light pulse to avoid interference among plural pulses, the repetition time, and the like are also determined by the structural design.

EXAMPLE 1

FIG. 2 illustrates Example 1 in which a terahertz time-domain spectroscopic system (THz-TDS) is configured by using the sensor device of Embodiment 1. Here, a femtosecond laser 20 containing optical fiber to emit an ultrashort pulse in femtoseconds is used as an excitation light source to split light into pump light 22 and probe light 23 through an optical splitter 21. Typically, a femtosecond laser of which the center wavelength is 1.55 μm, the pulse width is 20 fs, and the pulse repetition frequency is 50 MHz is used, but the wavelength may be in 1.06 μm band or the like, and the pulse width and the pulse repetition frequency are not limited to these values. The pump light 22 is coupled to a waveguide containing the above-mentioned electro-optic crystal 1 of the sensor device 24 according to the present invention. In that regard, a lens 25 is used, but a SELFOC (registered trademark) lens may be integrated by bonding the SELFOC lens to the incident end face of the sensor device 24. In this case, the application of non-reflecting coating to the end portion leads to reduction in Fresnel loss and reduction in unwanted interference noise. Alternatively, output of the femtosecond laser 20 may propagate through optical fiber (not illustrated) so that bonding is made as butt coupling to butt the fiber and the waveguide of the sensor device 24. In this case, an adhesive can be selected appropriately to reduce adverse effects of reflection. To split light, a fiber type can be used. When such a fiber portion that cannot maintain polarization is contained in the above fiber (not illustrated) or the femtosecond laser 20, it is desired that the polarization of incident light onto the sensor device 24 should be stabilized by an in-line polarization controller. Note that the excitation light source is not limited to the fiber laser. If the laser is not the fiber laser, measures taken to stabilize polarization and the like will be reduced.

As mentioned above, the generated terahertz wave propagates in the coupler of the sensor device 24 to enter a detector 29. When the photodetector is a photoconductive device with a dipole antenna formed in low-temperature grown GaAs, if the wavelength of excitation light from the light source 20 is 1.55 μm, unillustrated SHG crystal will be used to create a harmonic as probe light 23 of the detector 29. When the laser output is sufficient, a mixing phenomenon of two-photon absorption and middle level transition can lead to direct excitation with light of 1.55 μm without using the SHG crystal, which is practical. When the light source 20 is in 1 μm band, a fundamental can be used for probe light without creating the harmonic in the detector 29 of the photoconductive device made of an InGaAs single layer or MQW. Of course, a GaAs system can also be used in 1 μm band without the SHG crystal. In the system, for example, an optical chopper is arranged on the probe light side to modulate the light to enable synchronous detection using a signal acquiring section 26 for acquiring a detected signal through an amplifier (not illustrated) from the detector 29. Then, in a data processing/output section 28, a PC or the like is used to acquire the waveform of a terahertz signal while controlling an optical delay device 27 as a delay section to move. The delay section may be of any type as long as the delay section can adjust a delay time between the generation of a terahertz wave in the sensor device 24 and the detection of the terahertz wave in the detector 29 as detection means. The structure as mentioned above can detect a terahertz wave generated and propagated in the sensor device, and acquire information on a sample by analyzing terahertz light interacting with the sample placed on the sensor device 24. Thus, the system for sensing or imaging in the example includes the sensor device according to the present invention, a delay section for adjusting the delay time between the generation of a terahertz wave in the optical waveguide and the detection of the terahertz wave in the detector, a light source for generating light propagating in the optical waveguide, and a processing section for acquiring a terahertz wave signal interacting with a subject from output of the detector to perform processing.

The following will describe a case where DNA is used as the sample. DNA prepared in 0.5 μg/μl as liquid samples is used to attempt a structural determination of double strand (ds) and single strand (ss). The samples used are 5.4 kb circular double-stranded plasmid DNA and a single strand generated by heat-denaturing the DNA at 95 degrees Celsius for three minutes. In this case, though characteristic optical spectra are not observed, the samples can be sensed because the time intervals of the second and third pulses are different in FIG. 3 due to a difference in permittivity between the samples. When a terahertz wave is reflected on an interface with each sample, since the time is shifted by δt to reflect the permittivity of the sample, both Δt1 and Δt2 become longer by δt than those without samples. At this time, as mentioned above, since the first pulse is positioned at a constant time point independently of the samples, δt depending on the quantity and kind of each sample can be detected accurately. Actually, in this case of DNA samples, a difference between the single strand and the double strand can be determined by a quantity of about a few femtomoles.

The above describes the example of the determination of DNA samples by including the entire system configuration, but the femtosecond laser and the system used for the THz-TDS apparatus are not limited to those described here as long as signals of a time-domain spectroscopic system can be obtained. Further, a tablet, powder, a liquid solution, a tissue section, and the like, which can be placed to almost contact section with a total reflection region of the coupler (the meaning of "almost contact" is as mentioned above), can be measured as a sample. The determination method may be other than the method of making a determination from the time shifts of pulses in the example, such as to make a comparison in terms of amplitude variations in pulses or to perform Fourier transform on the pulses to perform spectral analysis. At this time, if the sample has a characteristic fingerprint spectrum, the component of the sample can be identified by a known method.

In the above example, the size of a sample is assumed to be the size placed in a region of about 1 mm. However, in the case of one reflection type, a sample of 100 μm or less can be sensed even if the sample is placed on the reflecting surface of the coupler. This is because, when the coupler is made of Si, the refractive index is 3.4 and this can form a pulse having a center frequency of 1 THz in the shape of a 100-μm spot or smaller on the reflecting surface due to the wavelength reduction effects. In that regard, a liquid reservoir structure (not illustrated) of about 100 μmφ may be made of resin or the like to prevent the sample from spreading peripherally or the sample may be supplied after an absorber into which the liquid sinks (such as a sponge-like structural zone having multiple minute pores, not illustrated) is arranged. In this case, a microscopic region can be sensed compared to sensing in normal space.

(Embodiment 2)

Figure 4A:
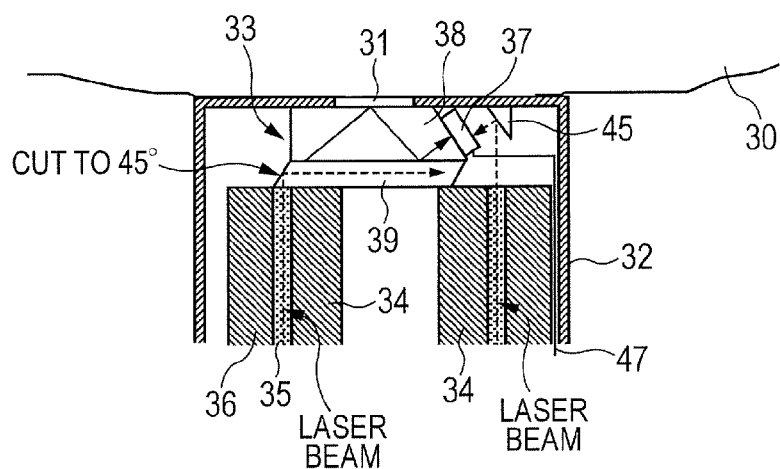
FIGS. 4A and 4B are structural diagrams of a sensor device according to Embodiment 2 of the present invention.
Figure 4B:
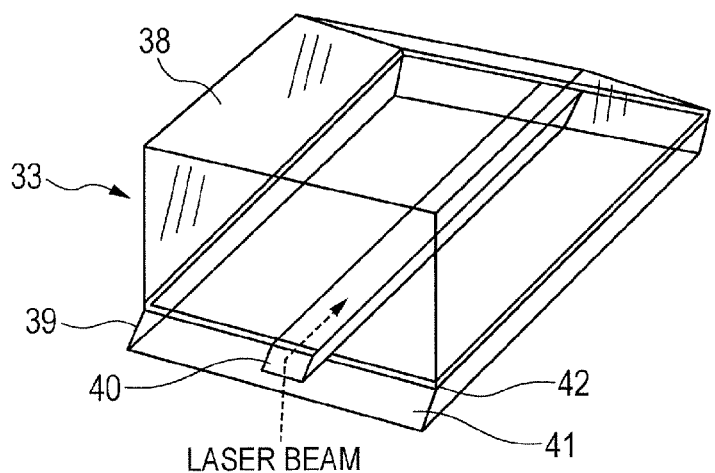
Figure 5:
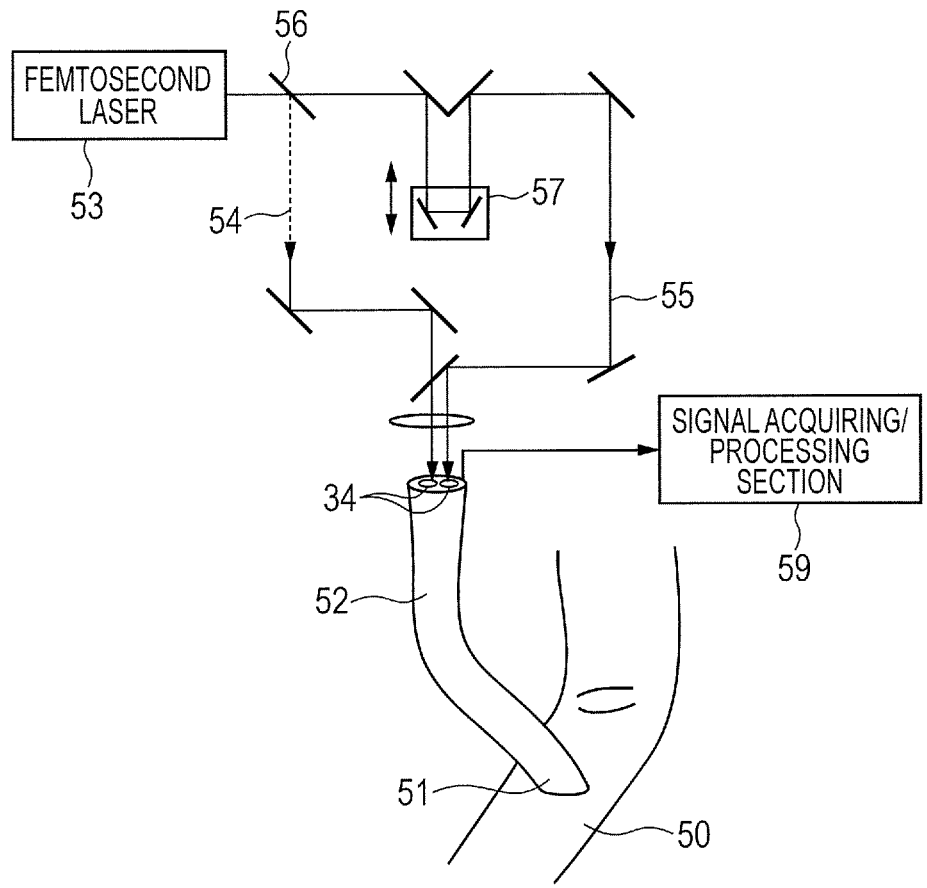
FIG. 5 is a diagram illustrating a general structure of Embodiment 2.

Embodiment 2 according to the present invention is to assemble a probe structure as illustrated in FIGS. 4A, 4B, and 5. The structure of a probe tip will be described with reference to FIGS. 4A and 4B. Here, an elongated structure is illustrated as a probe, but this shape can vary, such as the shape of a short column. FIG. 4A is a sectional view in which a window structure (aperture) 31 is provided at the tip of a probe outer frame 32 and pressed against the surface of a subject (sample) 30. The window structure is typically a round aperture of 100 μmφ in diameter, but the shape and size of the aperture are not limited thereto. Although the round aperture is generally suited to a case where the terahertz wave is non-polarized light, it can, of course, be applied to a case where the terahertz wave is polarized unidirectionally. On the other hand, a rectangular shape such as a square is suited to a case where the terahertz wave is polarized in a certain direction. Therefore, the aperture may be a rectangular aperture. The size is decreased as requirements for resolution performance increase. Thus, it is only necessary to set the size on a case-by-case basis. Further, the window structure may be a glass or resin plate the thickness of which is set properly so that an evanescent wave will penetrate into the outside. This makes the inside of the probe hermetically closed to prevent contaminations from the outside. In the lower part of the window structure 31, an optical waveguide 39 made up of electro-optic crystal and low refractive layers like in Embodiment 1, and a sensor device 33 made up of a coupler 38 for propagation of a terahertz wave are arranged to be pressed against the outer frame 32 by two pieces of optical fiber 34 each having a core 35 and a clad 36. It would be better to bond the entire structure after being assembled by an adhesive for mechanical stability.

In this embodiment, the structure is designed to reflect a terahertz wave once on a sensing surface (total reflection surface) up to a terahertz wave detector 37. The design principles are as described in Embodiment 1. The structure is designed according to the refractive indexes of materials used for the optical waveguide 39 and the coupler 38. Although this sensor device 33 may be of the same type as that in Embodiment 1, the optical waveguide here is of a ridge type, rather than a slab type, as illustrated in a perspective view of FIG. 4B to enhance the spatial resolution in order to improve output of the terahertz wave. The transverse structure of the optical waveguide can be so constructed that a surrounding region 41 is made by Ti diffusion to have a high refractive index and a waveguide core 40 is formed into a ridge shape by a method of providing a difference in refractive index or etching. A method of filling the surrounding region 41 with resin or the like may also be used. Further, a low refractive layer 42 is inserted between the coupler 38 and the core 40.

The width of the core is set, but not limited, to 4 μm to enable a single mode for propagating light. In the case of the ridge type, the generated terahertz wave is radiated from the optical waveguide in the traverse direction. The thickness of the coupler 38 is 150 μm and the length of the bottom face to contact with the optical waveguide is about 450 μm. The end face is cut to have an inner angle of 41 degrees (cut to exit vertically with respect to a Cherenkov angle of 49 degrees). The above window structure 31 is so set that the center will come to a point of one reflection. A face of the coupler 38 on the incident side of a laser beam is, but not limited to, normal to the direction of the optical waveguide as illustrated in FIGS. 4A and 4B as long as the angle does not affect the generated terahertz wave. Here, the thickness of the coupler 38 is made thin (150 μm) so that a radiation region of the terahertz wave from the ridge-shaped core 40 toward the window structure 31 should not be too large. This increases the spatial resolution. It is also desired that appropriate cut structures or non-reflecting coating be applied to the other end faces of the coupler 38 so that the reflection on the end faces will not affect the detected signals.

On the other hand, an end face of the optical waveguide 39 on which a laser beam is incident is cut to 45 degrees so that light from the core 35 of the optical fiber can be coupled as pump light. In other words, the optical waveguide 39 has a diagonal cut face for reflecting light to change the propagation direction of the light propagated from the outside in order to couple the light to the optical waveguide. It is also desired that even a terminal portion of the optical waveguide 39 be cut diagonally as illustrated in FIGS. 4A and 4B to avoid multiple reflections inside the optical waveguide 39, or be subjected to non-reflecting coating or surface roughening. Light from the other piece of fiber 34 is radiated to the detector 37 by means of a micromirror 45 to act as probe light.

Next, the general structure including the probe will be described with reference to FIG. 5. A laser beam from a femtosecond laser 53 is split by a beam splitter 56 into pump light 54 and probe light 55, and coupled to the two pieces of optical fiber 34 inside a terahertz wave probe 52. As described with reference to FIG. 4A, the optical fiber 34 is connected to a sensor device using a terahertz wave at a tip 51 of the terahertz wave probe 52. An optical delay system 57 is arranged to operate as THz-TDS like in Embodiment 1. The tip 51 of the terahertz wave probe 52 is pressed on a subject, e.g., an antebrachial region 50 of a human body to conduct an examination. An electric signal from a detector (e.g., the detector 37 in FIG. 4A) at the tip 51 is extracted to the outside through electric wiring 47 (see FIG. 4A) inside the terahertz wave probe 52, and processed in a signal acquiring/processing section 59. The processing method and the like are the same as those in Embodiment 1. Thus, the contact-type terahertz imaging probe of the embodiment includes the sensor device of the present invention with the aperture at one end to face a subject. Then, a waveguide for guiding a wave to this optical waveguide of the sensor device and electric signal wiring electrically connected to the detector of the sensor device are incorporated.

In FIG. 5, a spatial optical system is illustrated as the optical system for guiding light to the optical fiber 34, but the femtosecond laser 53 can be a fiber laser of an all-fiber type that connects the output to the terahertz wave probe 52 all the way through the fiber. In this case, an optical delay system inside the laser can be used as a time lag between pump light and probe light.

When the terahertz wave probe 52 is pressed on the antebrachial region 50 to conduct an examination, imaging is performed to assist in the diagnosis of cutaneous inflammation, disease, cancer, or the like. In this case, data on signal variations associated with a disease previously acquired is stored as a database to compare. Then, the comparison results are processed to enable high-speed imaging such as a determination on physical properties. Other than the observation of a disease, such a structure is also effective in the following case: When a transdermal drug is administered as a drug delivery system, the infiltration condition is observed in a non-destructive manner. Further, this structure can be applied to a case where the lining of an internal organ is observed by introducing an endoscope in the body and a case where tissues being treated during a surgery and the vicinity thereof are observed. In any of these cases, a window structure like in the embodiment can be used to perform terahertz imaging at a spatial resolution of the wavelength of a terahertz wave or less.

(Embodiment 3)

Figure 6:
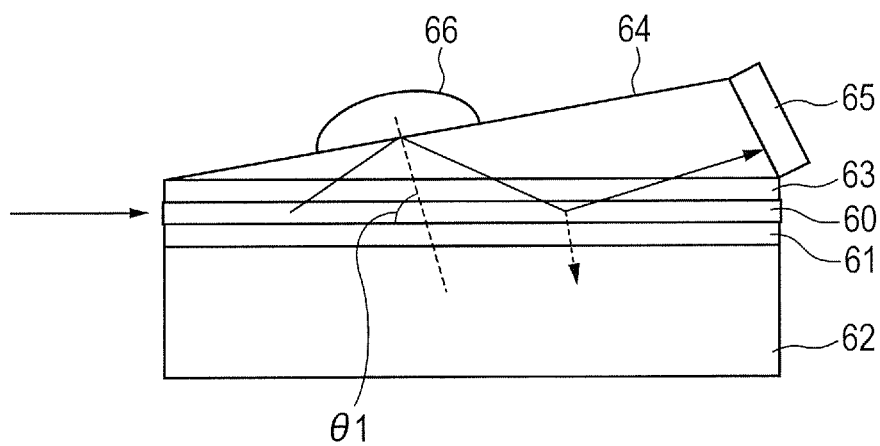
FIG. 6 is a structural diagram of a sensor device according to Embodiment 3 of the present invention.

Embodiment 3 according to the present invention is a modification to Embodiment 1. As illustrated in FIG. 6, an electro-optic crystal (e.g., MgO doped LN crystal) 60 and an optical waveguide made up of two low refractive layers 61 and 63 are arranged in the same way as in Embodiment 1. On the other hand, a coupler 64 for propagation of a terahertz wave has an inclination, and a crystal substrate (e.g., LN crystal) 62 of the same kind as the electro-optic crystal 60 of the optical waveguide to support the optical waveguide is provided. In other words, the total reflection section of the coupler 64 includes an inclined face that is not parallel to the optical waveguide. In some cases, the sensing surface of the coupler can have plural inclinations to be changed along the way. Further, the coupler may have both a face parallel to the optical waveguide and an inclined face. For example, the sensing surface may be so formed that a parallel plane is changed to an inclined plane halfway. The structure of the coupler 64 and the presence or the absence of the substrate 62 can be combined independently. For example, there is a case where the coupler is flat with a substrate, or a case where the coupler is inclined without any substrate.

In FIG. 6, in the case of LN crystal, since the refractive index to a terahertz wave is about 5.2, the terahertz wave partially goes through the underneath of the waveguides (60, 61, and 63) as illustrated in FIG. 6 (see the dotted line). As a result, the reflectivity to the Si coupler (refractive index 3.4) side is generally reduced, and this may reduce signal power. For example, when the coupler is parallel to the optical waveguide, if the Cherenkov angle is 49 degrees as in Embodiment 1, the incident angle to the substrate become 41 degrees as the complementary angle, resulting in a low reflectivity of about 9 percent. Note that this is a case where the thicknesses of the low refractive layers 61, 63 and the electro-optic crystal layer 60 are assumed to be thin compared with the terahertz wavelength.

On the other hand, for example, suppose that the sensing surface of the coupler is inclined as illustrated in FIG. 6 so that the incident angle to the substrate 62 can be set to about 70 degrees (see θ1=75 degrees in FIG. 6). In this case, if the terahertz wave is S-wave like in Embodiment 1 (where the Z axis in FIG. 1 is the electric field direction), a reflectivity of about 30 percent can be achieved. Such a structure can be applied to a case where the coupler is too thin to keep the strength or a case where the waveguides are created on the same crystal substrate to improve reliability. Thus, the inclination of the sensing surface of the coupler can be set to any angle within the scope of the present invention as long as terahertz propagation can occur properly in the coupler.

(Embodiment 4)

Figure 7:
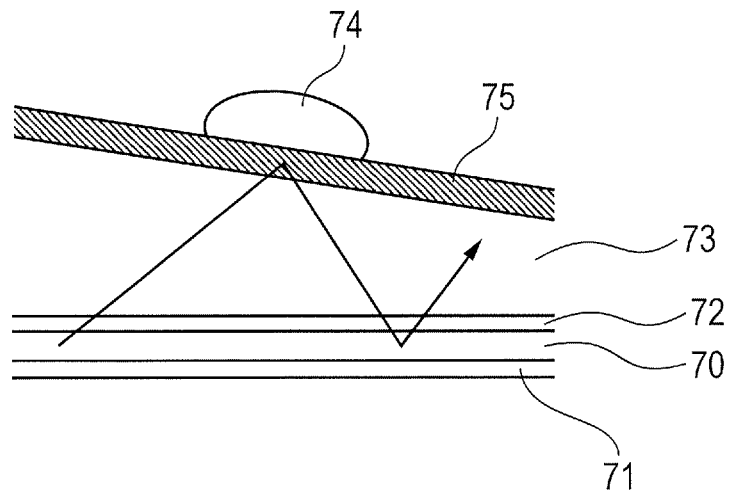
FIG. 7 is a structural diagram of a sensor device according to Embodiment 4 of the present invention.
Figure 8:
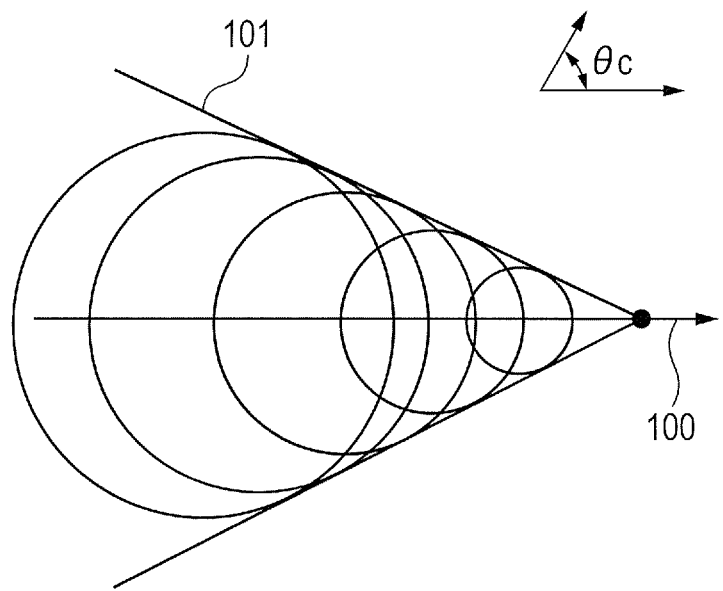
FIG. 8 is a conceptual diagram of electro-optic Cerenkov radiation.

Embodiment 4 according to the present invention is to arrange a conductive layer of metal or semiconductor having high electric conductivity on the top of the sensing surface in order to use the operation of a known plasmon sensor together. The plasmon sensor is a sensor using such a phenomenon that, when the conditions for adequate incident angle and refractive index to the total reflection surface are met, a surface plasmon resonance is induced to make a reflected wave decrease sharply. There are the Kretschmann configuration in which a conductive body is attached closely or arranged adjacent to the sensing surface to see the state of a subject on the conductive body, and the Otto configuration in which a sample is sandwiched between the sensing surface and the conductive body. FIG. 7 illustrates the former example.

FIG. 7 illustrates only the main part of the total reflection section. Since the other components such as the detector can be selected properly from the aforementioned embodiments, the illustration thereof is omitted. The sensing surface can be inclined beforehand as in Embodiment 3 to cause a plasmon resonance for a sample 74 to be examined. A coupler 73 is arranged adjacent to an optical waveguide containing an electro-optic crystal 70 and low refractive layers 71 and 72. For example, MgO doped LN crystal can be used as the electro-optic crystal 70 and Si can be used for the coupler 73. To implement the Kretschmann configuration, a conductive layer 75 is formed on the surface of the Si coupler 73 by ion implantation or the like. Instead of ion implantation, a metallic film may be formed by vapor deposition or the like to form this conductive layer. The sample 74 is placed in a region where a pulse of terahertz wave generated in the optical waveguide reaches at the Cherenkov angle, and is totally reflected so that the sample can be sensed. It should be noted that the case where the coupler is not inclined and other modifications such as the Otto configuration fall within the range of forms that can be carried out as the present invention.

In this embodiment, the attenuation extinction ratio of a terahertz wave signal to a sample having a specific refractive index can be increased to improve sensitivity.

In the aforementioned embodiments and examples, the description is mainly made by taking, as an example, the case where a femtosecond laser beam is used as excitation light to generate a pulse of terahertz wave by optical rectification. In contrast, a difference-frequency generation system for entering laser beams having two different oscillation frequencies $\upsilon 1$ and $\upsilon 2$ to output a monochromatic terahertz wave corresponding to the difference frequency may be employed. In this case, interference with the above-mentioned plural propagation paths occurs in places and beats of the terahertz waves are observed. Yet, since the terahertz waves interact with a subject in a manner as mentioned above to change the propagation state, changes in terahertz waves can be detected to acquire information on the subject. As the laser light source, Nd:YAG laser-excited KTP-OPO (Optical-Parametric-Oscillator) light source (which outputs two wavelengths of light) or two wavelength-variable laser diodes can be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-056533, filed on Mar. 13, 2012, which is hereby incorporated by reference herein in its entirety.

What is claimed is:

1. A sensor device comprising:
    an optical waveguide for propagating light, the optical waveguide containing an electro-optic crystal;
    a coupler for propagating a terahertz wave generated from the electro-optic crystal as a result of propagation of light in the optical waveguide; and
    a detector,
    wherein the coupler has a first face adjacent to the optical waveguide and a second face opposite to the first face and totally reflecting the terahertz wave generated from the electro-optic crystal, and
    wherein the detector detects the terahertz wave having a propagation state which varies in association with a subject placed on the second face, or the light having interacted with the terahertz wave having a varying propagation state.

2. The sensor device according to claim 1, wherein the sensor device is so designed that a terahertz wave generated from the electro-optic crystal will not interfere with a terahertz wave reflected by the second face.

3. The sensor device according to claim 1, wherein the light propagating through the optical waveguide is an ultrashort pulse in femtoseconds.

4. The sensor device according to claim 1, wherein the detector is arranged on a face of the coupler where the terahertz wave generated from the electro-optic crystal is not totally reflected.

5. The sensor device according to claim 1, wherein the optical waveguide has a diagonal cut face to change, by reflection, a propagation direction of light propagated from outside in order to couple the light to the optical waveguide.

6. The sensor device according to claim 1, wherein the second face includes a face that is not parallel to the optical waveguide.

7. The sensor device according to claim 1, wherein a conductive layer is attached closely to or arranged adjacent to the second face of the coupler, and a surface plasmon resonance is induced in the conductive layer.

8. The sensor device according to claim 1, wherein the optical waveguide contains the electro-optic crystal as a core portion for the light and low refractive layers as clad portions,
    at least one layer of the low refractive layers is sandwiched between the electro-optic crystal and the coupler, and
    a thickness d of the at least one layer fulfills:
    $a < d < \lambda_{eq}/10$,
    where a thickness that is $1/e^2$ of a light intensity of the propagating light in the electro-optic crystal (e is a base of natural logarithm) is denoted by a, and an equivalent wavelength in the at least one layer at a maximum frequency of the terahertz wave propagating in the coupler is denoted by $\lambda_{eq}$.

9. A contact-type terahertz imaging probe comprising the sensor device according to claim 1 with an aperture at one end to face a subject,
    wherein a waveguide for guiding light to an optical waveguide of the sensor device to guide a wave to the optical waveguide, and electric signal wiring electrically connected to a detector of the sensor device are incorporated.

10. A system for sensing or imaging, comprising:
the sensor device according to claim 1;
a delay section for adjusting a delay time between generation of a terahertz wave in the optical waveguide and detection of the terahertz wave in the detector;
a light source for generating light to propagate in the optical waveguide; and
a processing section for acquiring, from output of the detector, a signal of a terahertz wave interacting with the subject to perform processing on the signal.

11. A sensing method for a terahertz wave using the sensor device according to claim 1, comprising:
detecting, in the detector, a pulse signal of a terahertz wave that is not subjected to total reflection in the coupler and a pulse signal of a terahertz wave that is subjected to total reflection in the coupler;
comparing the signal that is not subjected to total reflection with the signal that is subjected to total reflection; and
acquiring, from a comparison result, information on a change caused by presence or absence of placement of a subject on a total reflection section of the coupler to acquire properties of the subject.

12. The sensor device according to claim 1, wherein the terahertz wave generated from the electro-optic crystal propagates as being totally reflected in the coupler.

13. The sensor device according to claim 1, wherein the second face almost contacts the subject.

14. The sensor device according to claim 1, wherein a film is arranged on the second face of the coupler, and the film has a thickness not greater than a penetration depth of an evanescent field of the terahertz wave generated from the electro-optic crystal.

15. The sensor device according to claim 1, wherein the light detected by the detector is light having propagated through the optical waveguide.

16. A sensor device comprising:
an optical waveguide into which light is introduced;
a region for placing a subject, the region being provided adjacent to a surface of the optical waveguide; and
a detector,
wherein the optical waveguide contains an electro-optic crystal which generates a terahertz wave when the light is introduced into the optical waveguide, and
wherein the electro-optic crystal has a refractive index which is higher for the light than for the terahertz wave generated from the electro-optic crystal.

17. The sensor device according to claim 16, wherein the detector is arranged in a region which is adjacent to a surface of the optical waveguide and is different from the region for placing the subject.

18. The sensor device according to claim 16, wherein the light contains two light components having different frequencies of $\upsilon 1$ and $\upsilon 2$ and the terahertz wave generated from the electro-optic crystal has a frequency of $|\upsilon 1-\upsilon 2|$.

19. The sensor device according to claim 16, wherein a film is arranged on the surface of the optical waveguide in the region for placing the subject, the film having a thickness not greater than an penetration depth of an evanescent field of the terahertz wave generated from the electro-optic crystal.

* * * * *